US010280450B2

(12) United States Patent
Levicky et al.

(10) Patent No.: US 10,280,450 B2
(45) Date of Patent: May 7, 2019

(54) DETECTION OF UNLABELED NUCLEIC ACIDS BY CHANGING SOLUBILITY OF SURFACE-ASSOCIATING PROBES

(71) Applicant: New York University, New York, NY (US)

(72) Inventors: Rastislav Levicky, Fairfield, CT (US); Wanqiong Qiao, Brooklyn, NY (US); Yatao Liu, Tustin, CA (US)

(73) Assignee: New York University, New York, NY (US)

( * ) Notice: Subject to any disclaimer, the term of this patent is extended or adjusted under 35 U.S.C. 154(b) by 485 days.

(21) Appl. No.: 14/540,668

(22) Filed: Nov. 13, 2014

(65) Prior Publication Data

US 2015/0141285 A1 May 21, 2015

Related U.S. Application Data

(60) Provisional application No. 61/903,885, filed on Nov. 13, 2013.

(51) Int. Cl.
*C12Q 1/68* (2018.01)
*C12Q 1/6816* (2018.01)

(52) U.S. Cl.
CPC .................. *C12Q 1/6816* (2013.01)

(58) Field of Classification Search
USPC ............. 435/6.1, 6.11, 6.12, 91.1, 91.2, 183, 435/283.1, 287.1, 287.2; 436/94, 501; 536/23.1, 24.3, 24.33, 25.3; 422/50, 68.1
See application file for complete search history.

(56) References Cited

U.S. PATENT DOCUMENTS 8,263,411 B2 9/2012 Levicky et al.
2004/0129571 A1* 7/2004 Onosato .................. C25D 5/12
205/160

OTHER PUBLICATIONS

Ouyang et al., Versatile Synthesis and Rational Design of Caged Morpholinos. J. Am. Chem. Soc, 131, 13255-13269, 2009.*
Paul Held, An Introduction to Fluorescence Resonance Energy Transfer (FRET) Technology and its Application in Bioscience. White Paper of BioTek. Published on Jun. 15, 2005.*
Liu, Y., Irving, D., Qiao, W., Ge, D. and Levicky, R. (2011) Kinetic mechanisms in morpholino-DNA surface hybridization. J. Am. Chem. Soc., 133, 11588-11596. Jan. 1, 2011.
Steemers, F.J., Ferguson, J.A. and Walt, D.R. (2000) Screening unlabeled DNA targets with randomly ordered fiber-optic gene arrays. Nat. Biotechnol., 18, 91-94. Jan. 1, 2000.
Yao, G. and Tan, W. (2004) Molecular-beacon-based array for sensitive DNA analysis. Anal. Biochem., 331, 216-223. Jan. 1, 2004.
Du, H., Disney, M.D., Miller, B.L. and Krauss, T.D. (2003) Hybridization-based unquenching of DNA hairpins on au surfaces: prototypical "molecular beacon" biosensors. J. Am. Chem. Soc., 125, 4012-4013. Jan. 1, 2003.

(Continued)

*Primary Examiner* — Frank W Lu
(74) *Attorney, Agent, or Firm* — Hodgson Russ LLP

(57) ABSTRACT

Provided are methods and devices for detection of unlabeled nucleic acids. The detection methods are based on change of solubility of hydrophobic probes upon hybridization with a polynucleotide. In one embodiment, the probes are morpholino probes, having a fluorophore attached thereto. The morpholino probes are immobilized on a substrate that has fluorescence quenching functionality.

12 Claims, 13 Drawing Sheets

Specification includes a Sequence Listing.

(56) References Cited

OTHER PUBLICATIONS

Stoermer, R.L., Cederquist, K.B., McFarland, S.K., Sha, M.Y., Penn, S.G. and Keating, C.D. (2006) Coupling molecular beacons to barcoded metal nanowires for multiplexed, sealed chamber DNA bioassays. J. Am. Chem. Soc., 128, 16892-16903. Jan. 1, 2006.

Huang, C., Stakenborg, T., Cheng, Y., Colle, F., Steylaerts, T., Jans, K., Van Dorpe, P. and Lagae, L. (2011) Label-free genosensor based on immobilized DNA hairpins on gold surface. Biosens. Bioelectron., 26, 3121-3126. Jan. 1, 2011.

Brown, L.J., Cummins, J., Hamilton, A. and Brown, T. (2000) Molecular beacons attached to glass beads fluoresce upon hybridisation to target DNA. Chemical Communications, 621-622. Jan. 1, 2000.

Piestert, O., Barsch, H., Buschmann, V., Heinlein, T., Knemeyer, J.-P., Weston, K.D. and Sauer, M. (2003) A Single-Molecule Sensitive DNA Hairpin System Based on Intramolecular Electron Transfer. Nano Letters, 3, 979-982. Jan. 1, 2003.

Du, H., Strohsahl, C.M., Camera, J., Miller, B.L. and Krauss, T.D. (2005) Sensitivity and Specificity of Metal Surface-Immobilized "Molecular Beacon" Biosensors. J. Am. Chem. Soc., 127, 7932-7940. Jan. 1, 2005.

\* cited by examiner

Covalent Immobilization – Thiol-terminated Oligonucleotides

DETECTION OF UNLABELED NUCLEIC ACIDS BY CHANGING SOLUBILITY OF SURFACE-ASSOCIATING PROBES

CROSS-REFERENCE TO RELATED APPLICATIONS

This application claims priority to provisional patent application No. 61/904,885, filed Nov. 13, 2013, the disclosure of which is incorporated herein by reference.

STATEMENT REGARDING FEDERALLY-SPONSORED RESEARCH

This invention was made with government support under grant number RO1 HG004512 from the National Institutes of Health. The government has certain rights in the invention.

BACKGROUND OF THE DISCLOSURE

Surface hybridization is a reaction in which nucleic acid analyte, or "target", molecules present in solution bind to "probe" strands immobilized on a solid support due to associations between nucleic bases on the probe and target strands. Surface hybridization plays a key role in a number of bioanalytical techniques, including DNA microarrays and sequencing technologies. In diagnostic applications the extent of probe-target association is usually quantified by "labeling" of the target analyte, or of the hybridized probe/target complex, through covalent or physical association with a molecular moiety designed to facilitate detection. Examples of such moieties include fluorophores, radiolabels, chemiluminescent labels, and electrochemically-active labels, resulting in signals based in light (fluorescence, luminescence), radioactivity, or current that can be correlated with the extent of surface hybridization. On the other hand, detection of unlabeled, and thus unaltered, samples can decrease assay costs, simplify preparation of the sample, decrease experimental variability, and avoid possible alteration of the probe-target interaction. For example, use of folded DNA probes such as hairpins, molecular beacons, and surface-quenched beacons can detect unlabeled targets through a change in conformation of the folded probe that results in emission of fluorescence or altered charge transfer characteristics, depending on the type of probe used. In these instances, the requirement is to design a specific probe sequence that folds differently in the absence and presence of the target. While they enable detection of unlabeled samples, a disadvantage of such folded probes is the requirement for a specific conformation in the unhybridized state, which introduces extra design steps, requires optimization of the folding thermodynamics, and results in introduction of additional nucleotides into the probe that can compromise accuracy with which target sequences are recognized.

SUMMARY OF THE DISCLOSURE

The present disclosure provides methods and devices for detection of unlabeled nucleic acids. The detection methods are based on change of solubility of probes upon hybridization. In one embodiment, the probes are morpholino probes. The present disclosure also provides devices useful for detection according to the methods provided herein.

In one embodiment, this disclosure provides a method for detecting in a test sample the presence or absence of polynucleotide strands having a sequence of interest. In one embodiment, the polynucleotide strands that are to be detected in the test sample are not labeled. The method comprises providing a substrate that has fluorescence quenching functionality and that has immobilized thereon, a plurality of the hydrophobic capture strands (such as morpholino strands), each strand having a fluorophore attached thereto, wherein the hydrophobic capture strand has a sequence that is complementary to the sequence of the polynucleotide strands comprising the sequence of interest; contacting the substrate with a test sample in an aqueous medium; and measuring if there is an increase in fluorescence (unquenching), wherein an increase in fluorescence over control (base fluorescence prior to contacting with the test sample, or fluorescence from sample known not to contain the particular polynucleotide strand) is indicative of the presence of the specific polynucleotide strands in the test sample.

In one embodiment, the hydrophobic capture strands are attached at or toward one end to the substrate and the other end is free, and the hydrophobic capture strand has a fluorophore attached to it toward its free end or at the free end. In one embodiment, the hydrophobic capture strands are morpholino strands attached to the substrate at or toward one end and have fluorophore attached toward or at the free end.

In one embodiment, the quenching functionality of the substrate is provided by having a conducting substrate, a non-conducting substrate having a conducting surface layer, or a conducting or non-conducting substrate having fluorescence-quenching molecules attached thereto.

In the absence of hybridization, the fluorophores attached toward or at the free end of the hydrophobic capture strands (e.g., morpholino strands) are in proximity to the substrate such that the fluorescence of the fluorophore is quenched by the quenching functionality of the substrate. Upon hybridization of a polynucleotide strand to the hydrophobic capture strand, the hybridized strands are rendered hydrophilic and therefore, the fluorophore becomes sufficiently spatially separated from the quenching functionality of the substrate resulting in an increase in detectable fluorescence due to unquenching.

In one aspect, this disclosure provides a substrate (conducting or non-conducting) that has hydrophobic capture strands (such as morpholino molecules) attached thereto. The hydrophobic capture strands are attached at or toward one end to the substrate and have fluorophores attached at or toward the free end. If the substrate is non-conducting, it has a conducting layer on its surface and/or has fluorescence quenching molecules attached to its surface.

In one aspect, this disclosure provides a device for detecting polynucleotide sequences, said device comprising a substrate that can provide fluorescence quenching functionality and that has immobilized thereon a plurality of hydrophobic capture strands (such as a morpholino molecule) having a desired sequence, each strand having a fluorophore attached thereto. The quenching functionality may be provided by the substrate itself when it is a conducting substrate (such as gold, etc.) or may be provided by a non-conducting substrate (such as glass, etc.) which has a conducting layer on its surface, and/or has fluorescence quenching molecules attached thereto.

The instant methods and devices can be used to identify the presence of nucleic acid sequences of interest in a complex mixture of sequences, such as in genetic testing, pathogen detection, cancer diagnosis and the like.

DETAILED DESCRIPTION OF THE DISCLOSURE

Morpholino (MO) probes are synthetic analogues of DNA that possess an uncharged backbone, and thus a lowered solubility in aqueous solutions. Because of their lowered solubility, MOs immobilized on a solid support do not become well solvated when this support is placed into an aqueous solution. On the other hand, hybridization with nucleic acid analyte introduces charge to the MO/target complex, rendering this complex significantly more soluble. The instant methods and devices use this change in solubility between the unhybridized and hybridized states of an immobilized MO probe to detect unlabeled targets through unquenching of fluorescence without the need for the design of probe sequences that fold into a specific conformation. In the instant methods and using the instant devices, detection is implemented by depositing a fluorophore-modified morpholino probe on a solid support that is capable of quenching the fluorophore, either through its intrinsic properties (e.g. gold) or through modification (e.g., surface modifications) with groups or materials that are capable of fluorescence quenching (referred to herein as "fluorescence quenchers", "quenchers" or "fluorescence quenching materials"). In the unhybridized state the probe lies on the support, due to its low solubility, so that its fluorescence is quenched. When hybridization takes place, the probe/target complex becomes more soluble and, because of the improved solubility, will be spatially separate from the substrate and will extend further into the solution. This transition to a more solvated state will therefore be accompanied by increased spatial separation of the probe fluorophore from the solid support, increasing fluorescence and leading to detection of hybridized targets. This "un-quenching" method provides a route to detection of unlabeled samples.

In one aspect, this disclosure provides a method for detecting the presence or absence of hybridization of a polynucleic acid. The detection method uses one or more hydrophobic capture strand immobilized on a substrate, which is either a conducting substrate such that it can act a quencher of fluorescence or is a non-conducting substrate in which case there are quencher molecules immobilized on the non-conducting substrate. Any probe capable of undergoing an unqueching transition without the need for a specific base sequence or secondary structure into the probe can be used. An example is morpholino probes. Another example is peptide nucleic acids (PNA) probes. In one embodiment, the probes are such that they undergo an unquenching transition in response to a solubility change induced by hybridization.

Figure 1:
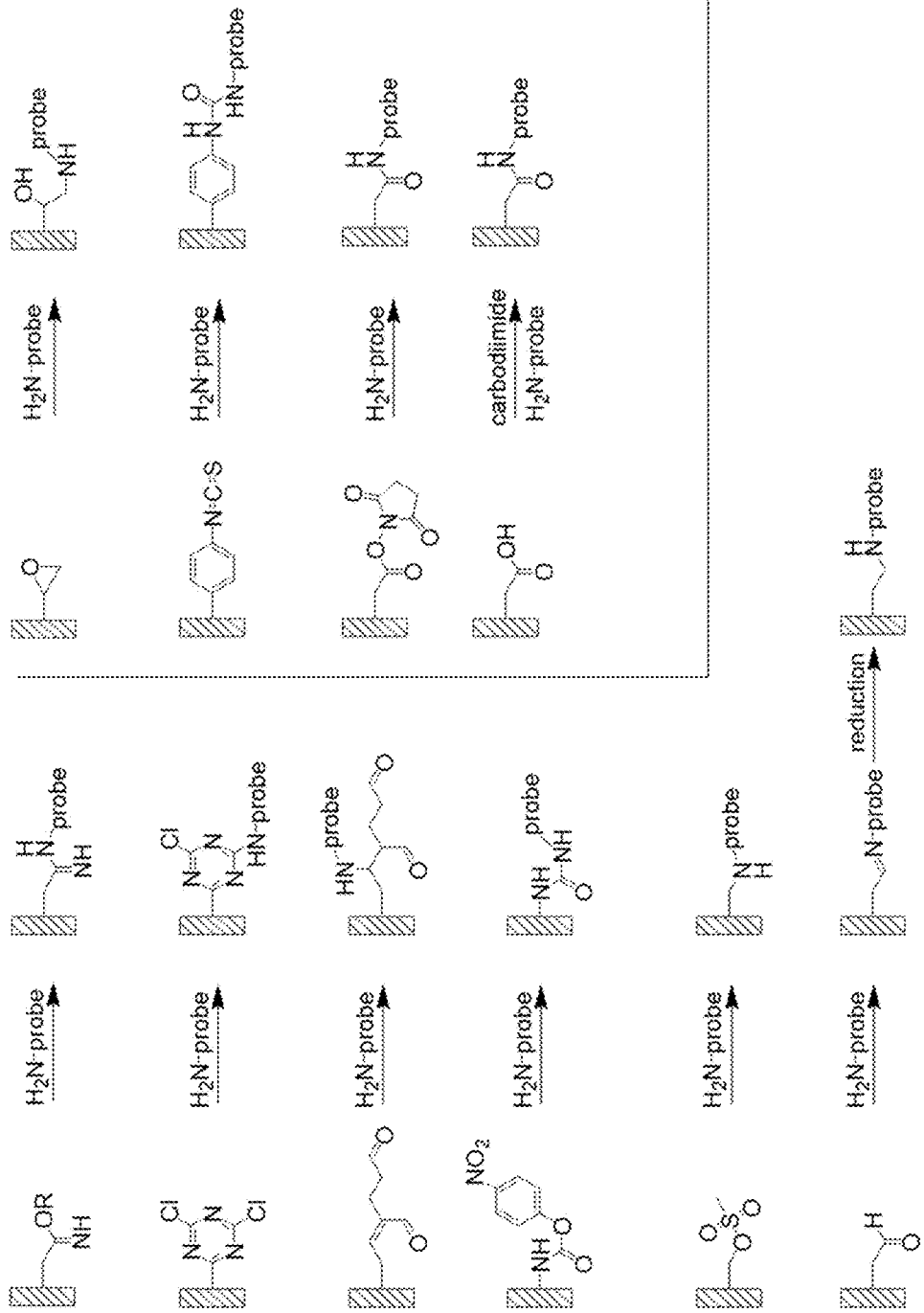
FIG. 1 is a representation of different chemistries useful for covalent immobilization using amine-terminated hydrophobic capture strands (HCS), referred to as "probe" in the figure.
Figure 2:
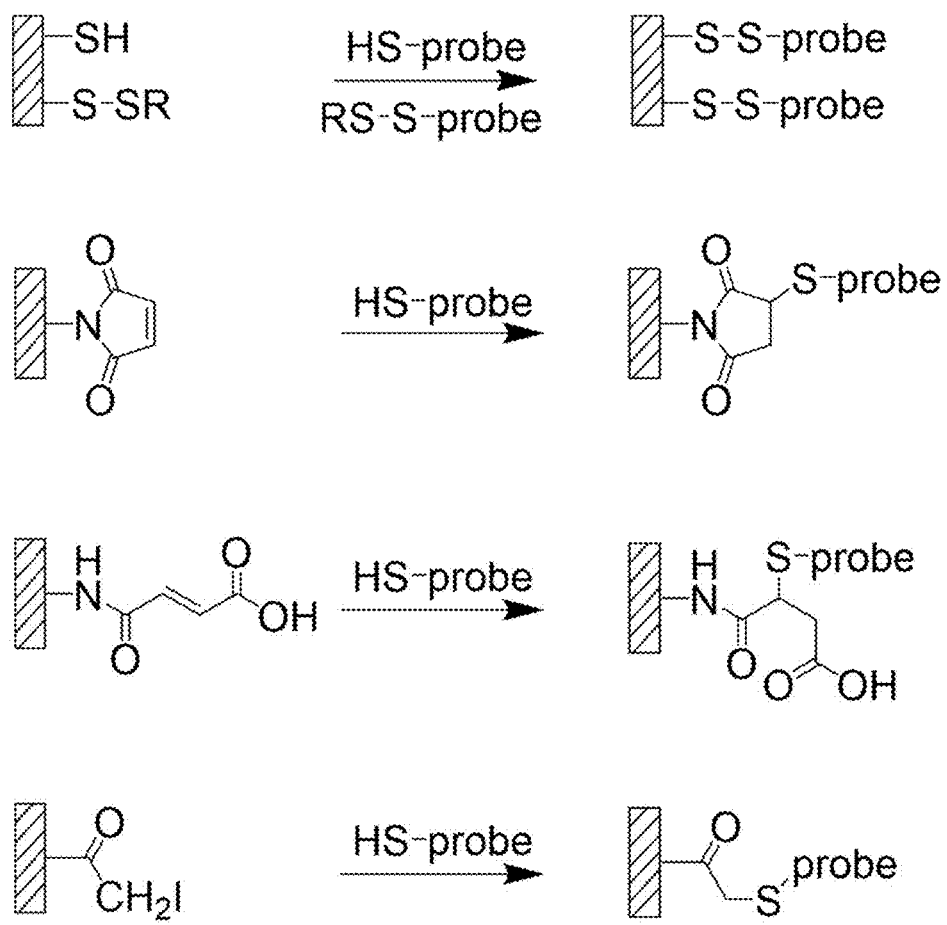
FIG. 2 is a representation of different chemistries useful for covalent immobilization using thiol-terminated HCS probes.

The substrate may be conducting. Examples include metals (such as gold), graphene, carbon nanotubes, glassy carbon, indium tin oxide, and the like. The substrate may by non-conducting. Examples include alumina, glasses, silicon dioxide, polymers, and the like. A variety of surface chemistries can be used to immobilize the capture strand and/or the quenching molecules on the substrate (e.g., covalent immobilization and physical immobilization). Such surface chemistries are known to those skilled in the art. (For example, see Cass et al., 1998, Immobilized Biomolecules in Analysis. New York, Oxford University Press Inc.) Examples of suitable chemistries are provided in the figures in this disclosure. FIGS. 1 and 2 provide examples of suitable covalent immobilization of the hydrophobic capture strands. In these figures "probe" represents hydrophobic capture strands.

Various quenchers and fluorophores are also known in the art. For example, see Marras et al., Interactive Fluorophore and Quencher Pairs, Mol. Biotechnol, 38(3):247-55, 2008, incorporated herein by reference.

Examples of suitable fluorophores include those listed in the following Table 1.

TABLE 1

Fluorophore labels for fluorescent hybridization probes

| Fluorophore | Alternative Fluorophore | Excitation (nm) | Emission (nm) |
|---|---|---|---|
| FAM | | 495 | 515 |
| TET | CAL Fluor Gold 540[A] | 525 | 540 |
| HEX | JOE, VIC[B], CAL Fluor Orange 560[A] | 535 | 555 |
| Cy3[C] | NED[B], Quasar 570[A], Oyster 556[D] | 550 | 570 |
| TMR | CAL Fluor Red 590[A] | 555 | 575 |
| ROX | LC red 610[E], CAL Fluor Red 610[A] | 575 | 605 |
| Texas red | LC red 610[E], CAL Fluor Red 610[A] | 585 | 605 |
| LC red 640[E] | CAL Fluor Red 635[A] | 625 | 640 |
| Cy5[C] | LC red 670[E], Quasar 670[A], Oyster 645[D] | 650 | 670 |
| LC red 705[E] | Cy55[C] | 680 | 710 |

[A]CAL and Quasar fluorophores are available from Biosearch Technologies,
[B]VIC and NED are available from Applied Biosystems,
[C]Cy dyes are available from Amersham Biosciences;
[D]Oyster fluorophores are available from Integrated DNA Technologies; and
[E]LC (Light Cycler) fluorophores are available from Roche Applied Science.

Examples of suitable quencher molecules include those listed in the following Table 2.

TABLE 2

Quencher labels for fluorescent hybridization probes

| Quencher | Absorption Maximum (nm) |
|---|---|
| DDQ-I[A] | 430 |
| Dabcyl | 475 |
| Eclipse[B] | 530 |
| Iowa Black FQ[C] | 532 |
| BHQ-1[D] | 534 |
| QSY-7[E] | 571 |
| BHQ-2[D] | 580 |
| DDQ-II[A] | 630 |
| Iowa Black RQ[C] | 645 |
| QSY-21[E] | 660 |
| BHQ-3[D] | 670 |

[A]DDQ or Deep Dark Quenchers are available from Eurogentec;
[B]Eclipse quenchers are available from Epoch Biosciences;
[C]Iowa quenchers are available from Integrated DNA Technologies;
[D]BHQ or Black Hole quenchers are available from Biosearch Technologies; and
[E]QSY quenchers are available from Molecular Probes.

Morpholino probes can be obtained from commercial sources (such as Gene Tools). The hydrophobic capture strands (such as MO probes) may be immobilized on the substrate by spotting. For example, MO probes can be spotted onto commercially available substrates using standard printing equipment. Each probe may be spotted multiple times. In one embodiment, concentration for spotting ranges from 1 micromolar to 100 micromolar including all inter values and ranges therebetween. In one embodiment, the spots have a width of 10 microns to 1 millimeter including all inter values and ranges therebetween. In one embodiment, inter-spot distance is from 0 to 1 millimeter. In one embodiment, the inter-spot distance is 0.1 to 1 millimeter including all values to the tenth decimal place and ranges therebetween. After printing, the non-specifically adsorbed probes are removed by washing.

In one embodiment, two or more sets of capture strands are immobilized on the substrate. Each set comprises capture strands with a unique sequence and unique fluorophore. Thus, all strands within a set have the same sequence and same fluorophore. Such sets of capture strands can be used to detect multiple polynucleotide sequences in a sample. The substrate may have multiple quenchers specific to each of the fluorophores. In one embodiment, two or more sets of morpholinos and fluorophores may be present in the same spot or may be present in discrete spots.

In contrast to not having to design a folded motif (as in molecular beacons, surface-quenched beacons, or Smart Probes, the present methods work with any arbitrary probe sequence. Thus, it is not necessary to design probes with appropriate folding conformations, folding/unfolding thermodynamics, or GC content. Because any probe sequence will work, probes can be selected based purely on criteria of optimizing detection of the desired target sequence. The instant methods and devices simplify probe design as well as avoids introduction of additional nucleotides into the probes that, in the case of folded-probe types, can interfere with specificity of hybridization to the target of interest. Thus, the present capture strands do not need to have, and in one embodiment, do not have, regions that can base pair within the strand (e.g., to form a hairpin structure).

Typical hybridization conditions involve probes that are 15 to 100 bases/nucleotides in length (including all integer values therebetween), with shorter (typically less than 25 bases/nucleotides) sequences affording greater specificity to mismatched bases in target strands, while longer sequences (typically more than 25 bases/nucleotides) improve detection of low concentration targets and enhance specificity to a particular genomic target such as mRNA or cDNA from a gene of interest. In one embodiment, the probes have from 20 to 50 bases, including all integer values therebetween). In one embodiment the probes have 25 bases. Hybridizations can be performed from conditions involving no added salt to high salt concentrations of around one molar. Very low to no salt conditions are possible because morpholino probes can hybridize with DNA or RNA target strands even in the absence of added salt. In one embodiment, hybridization is performed in the absence of salt.

Hybridization in the present method between the morpholino strand and the test polynucleotide strand can be carried out under low salt or high salt conditions. In one embodiment, the present method is carried out in low salt concentration. In one embodiment, there is no salt in the reaction mixture (i.e., aqueous medium). In one embodiment, the salt concentration is from 0 to 0.01 mM (and all values to the hundredth decimal place and ranges therebetween). In one embodiment, the salt concentration of the reaction mixture is from 0.01 mM to 1 M (and all integers to the hundredth decimal place and ranges therebetween). In one embodiment, the salt concentration is from 0.1 to from 1 mM (and all values to the tenth decimal place and ranges therebetween). In one embodiment, the salt concentration is from 1 mM to 100 mM (and all integers and ranges therebetween. Hybridization to DNA probes is inefficient at low salt concentrations. Therefore, low salt concentration in the present method is useful because it is expected to reduce hybridizations of DNA strands within the sample thereby improving efficiency of detection by increasing availability for hybridization to the morpholino strands on the substrate.

In one embodiment, this disclosure provides a method for detecting the presence or absence of one or more specific polynucleotide strands in a sample. The method comprises: a) providing a substrate that can provide fluorescence quenching functionality and has immobilized thereon, a plurality of the hydrophobic capture strands, each strand having a fluorophore attached thereto and comprising the desired sequence, wherein the substrate has a base fluorescence (representing a quenched level of fluorescence); b) contacting the substrate with a test sample in a aqueous medium (such as a phosphate buffer); and c) measuring if there is an increase in fluorescence (unquenching), wherein an increase in fluorescence over the base fluorescence is indicative of the presence of the specific polynucleotide strands in the sample (i.e., polynucleotide strands that are complementary to the hydrophobic capture strands).

In one embodiment, the hydrophobic capture strands are attached at one end (a first end or terminus) to the substrate and the other end (a second end or terminus) is free, and the hydrophobic capture strand has a fluorophore attached to it toward its free end or at the free end. In one embodiment, the hydrophobic capture strands are morpholino strands attached to the substrate at one end and having a fluorophore attached at the free ends.

In one embodiment, the quenching functionality of the substrate is provided by having a conducting substrate. In one embodiment, the quenching functionality is provided by having a non-conducting substrate that has a surface layer (partial or complete) of conducting material on its surface or has quencher molecules attached thereto.

In the absence of hybridization, the fluorophores attached to the free end of the hydrophobic capture strands (e.g., morpholino strands) are in proximity to the substrate such that the fluorescence of the fluorophore is quenched by the fluorescence quenching functionality of the substrate. Upon hybridization of a polynucleotide strand to the hydrophobic capture strand, the hybrid is rendered hydrophilic and due to its increased solubility in the aqueous medium, the fluorophore becomes sufficiently separated from the fluorescence quenching functionality of the substrate to result in an increase in detectable fluorescence due to unquenching.

In one embodiment, this disclosure provides a method for detecting the presence or absence of hybridization of a polynucleotide strand to a hydrophobic capture strand (such as a morpholino) having a desired sequence comprising the steps of: a) contacting in an aqueous medium a sample suspected of containing a polynucleotide strand that can hybridize to the hydrophobic capture strand with a non-conducting substrate that has immobilized thereon: i) a plurality of the hydrophobic capture strands, each strand having a fluorophore attached thereto and comprising the desired sequence; and ii) a plurality of fluorescence quenching molecules, wherein prior to contacting the hydrophobic capture strands with polynucleotides sequences that can hybridize with the hydrophobic capture strand, in an aqueous medium, the hydrophobic capture strands are in proximity to the substrate such that the fluorescence of the fluorophores is quenched, and upon hybridization of the polynucleotide strand to the hydrophobic capture strand the hybridized hydrophobic capture strand-polynucleotide strand is rendered hydrophilic such that fluorescence from the fluorophore is now unquenched, wherein the location of the fluorophore on the hydrophobic capture strand is such that upon hybridization of a the polynucleotide strand to the hydrophobic capture strand the fluorophore is sufficiently separated from the quencher molecule to result in an increase in detectable fluorescence; and b) measuring the fluorescence of the fluorophores, wherein an increase in the fluorescence of the fluorophores relative to the fluorescence of a control is indicative of hybridization of the polynucleotide strand to the capture strand, and a lack of increase in the fluorescence of the fluorophores relative to the control is indicative of the absence of hybridization of the polynucleotide strand to the capture strand.

In one embodiment, this disclosure provides a method for detecting the presence or absence of hybridization of a polynucleotide strand to a hydrophobic capture strand (such as a morpholino) having a desired sequence comprising the steps of: a) contacting in an aqueous medium a sample suspected of containing a polynucleotide strand that can hybridize to the hydrophobic capture strand with a conducting substrate that has immobilized thereon a plurality of the hydrophobic capture strands, each strand having a fluorophore attached thereto and comprising the desired sequence, wherein prior to hybridization of the hydrophobic capture strand and the polynucleotide the fluorophore on the hydrophobic capture strand is in proximity to the substrate such that the fluorescence of the fluorophores is quenched, and upon hybridization of a the polynucleotide strand to the hydrophobic capture strand, the hybridized hydrophobic capture strand-polynucleotide strand is rendered hydrophilic and is sufficiently separated from the conducting substrate to result in an increase in detectable fluorescence; and b) measuring the fluorescence of the fluorophores, wherein an increase in the fluorescence of the fluorophores relative to the fluorescence of a control is indicative of hybridization of the polynucleotide strand to the hydrophobic capture strand, and a lack of increase in the fluorescence of the fluorophores relative to the control is indicative of the absence of hybridization of the polynucleotide strand to the hydrophobic capture strand. The control may be the base fluorescence prior to contact with a test polynucleotide or may be the fluorescence after contacting with a negative control (i.e., which does not have the polynucleotide that will hybridize to the hydrophobic capture strand).

In one aspect, this disclosure provides a device for detecting polynucleotide sequences, said device comprising a non-conducting substrate, which has immobilized thereon: a) a plurality of hydrophobic capture strands comprising a desired sequence, each strand having a fluorophore attached thereto and being attached to the substrate at substantially one end of the strand; and b) a plurality of quencher molecules, wherein the fluorophore is located on the strand such that upon hybridization of a polynucleotide strand to the hydrophobic capture strand the fluorophore is sufficiently separated from the quencher molecules to result in a detectable increase in fluorescence of the fluorophore.

In one embodiment, this disclosure provides a device for detecting polynucleotide sequences, said device comprising a conducting substrate that can quench the fluorescence of a fluorophore, said substrate having immobilized thereon: a plurality of hydrophobic capture strands, each strand comprising a desired sequence and having a fluorophore attached thereto, and each strand being attached to the substrate at substantially one end of the strand, wherein the fluorophore is located on the strand such that upon hybridization of a polynucleotide strand to the hydrophobic capture strand the fluorophore is sufficiently separated from the conducting substrate to result in a detectable increase in the fluorescence of the fluorophore.

In one embodiment, this disclosure provides a device for detecting polynucleotide sequences, said device comprising a substrate which can provide fluorescence quenching functionality and which has immobilized thereon a plurality of hydrophobic capture strands comprising a desired sequence, each strand having a fluorophore attached thereto. In one embodiment, the hydrophobic capture strand is a morpholino. In one embodiment, the hydrophobic capture strand (e.g., a morpholino strand) is attached to the substrate at one end has a fluorophore attached toward the free end or at the free end. In one embodiment, the quenching functionality is provided by the substrate being a conducting substrate (such as gold etc.). In one embodiment, the quenching functionality is provided by the substrate being a non-conducting substrate (such as glass etc.) which has a conducting layer on its surface. In one embodiment, the quenching functionality is provided by quencher molecules attached to the substrate—which may be conducing or non-conducting. In one embodiment, at least 5 bases separate the fluorophore from the conducting substrate. In one embodiment, 5, 6, 7, 8, 9, 10 or more bases separate the fluorophore on the morpholino from the substrate.

The instant methods and devices can be used to identify the presence of unlabeled nucleic acid sequences of interest in a complex mixture of sequences. The most direct applications of these methods and devices are in biosensor type applications, in basic life science research, and in clinical diagnostics. For example, the methods enable simpler approaches to detection and identification of unlabeled nucleic acid sequences for purposes of genetic testing, pathogen detection, or cancer diagnosis.

The following example is presented to further illustrate the invention and is not intended to be limiting.

Example 1

This example provides an illustration of a novel un-quenching approach to detecting unlabeled analyte molecules. The un-quenching approach was based on a variation in conformation of MO probes before and after hybridization.

Figure 3:
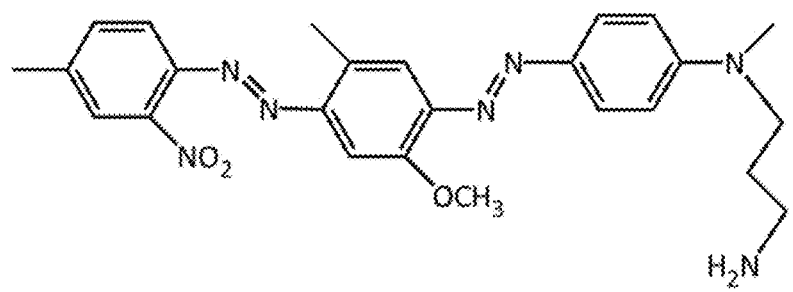
FIG. 3 is a representation of the structure of Amine-Black Hole Quencher (BHQ)-1.

Materials and Methods. Morpholino probes were ordered from Gene Tools LLC, and DNA probes were from Integrated DNA Technologies. MO and DNA concentrations were confirmed spectrophotometrically before each use. To optimize TIRF settings, single-stranded DNA targets labeled with Cy5 fluorophores at their 3' end were hybridized to MO probes (5'-NH$_2$-GTAGCTAATGATGTGGCATCGGTTG) (SEQ ID NO:1) in 0.11 mol L$^{-1}$ pH 7.0 sodium phosphate buffer. For development of the un-quenching approach to detection, MO probes were in addition end-modified with a fluorescein dye (absorbance $\lambda_{max}$=495 nm, emission $\lambda_{max}$=520 nm) at the 3' end. The probe sequence was also shifted by one base position to mitigate guanine-based quenching of fluorescein, yielding the sequence 5'-NH$_2$-TAGCTAATGATGTGGCATCGGTTGC (SEQ ID NO: 2)-Fluorescein. The targets were the fully complementary DNA oligos without any modification or labeling. Black hole quencher 1 (BHQ-1, Absorbance $\lambda_{max}$=534 nm) dye was purchased modified with an amine group (FIG. 3) from Biosearch Technologies. All probes and targets were diluted with deionized water (18.2 MΩ cm) to 200 μmol L$^{-1}$ before storage at −20° C.

Microarray Fabrication. MO probes were spotted onto commercial aldehyde slides on a XactII™ contact printing system (Lab Next Inc., Glenview, Ill.) using Xtend microarray pins. Each probe was spotted multiple times at a spotting concentration of 10 μmol L$^{-1}$ in 0.1 mol L$^{-1}$ pH 9.0 sodium phosphate buffer unless otherwise specified. This printing condition provided MO spots width a diameter of 300 μm or 100 μm based on the printing dimensions of two different sized pins. After printing, the slides were dried overnight (22 hours) at 25° C. and a humidity of 30% or less. Following overnight incubation, slides were washed to get rid of non-specifically adsorbed probes. Slides were dried under a nitrogen stream.

TIRF Measurements. Microarray slides were mounted on a TIRF stage that coupled the incident laser beam into the MO microarray slide through its side. The stage together with a flow cell were obtained from TIRF Technologies Inc (Morrisville, N.C.). A home built Peltier temperature-control module was used for temperature control and monitoring. The excitation laser wavelength used was 473 nm (for fluorescein) or 640 nm (for Cy5 dyes). Lasers were provided by Laserglow Technologies (Toronto, Canada). The emitted fluorescent signal first went through a 510-560 nm or a 650-690 nm bandpass filter (Omega Optical Inc., Brattleboro, Vt.) and was then detected by an EMCCD camera (Andor Technology, Belfast, UK) with exposure time set to 1 second. The electron multiplier (EM) gain was set according to needs of the experiment. Different from the procedures described in Chapter III, the hybridization was followed in real-time. For TIRF imaging, buffer with targets was not rinsed off prior to detection, thus also eliminating any artifacts from washing and drying.

TIRF Image Analysis. Image analysis was carried out by Andor SOLIS software (Andor Technology, Belfast, UK) using a home-written And or Basic program with the location of spots acquired directly from the image. Spot intensities were extracted from TIRF images. For each spot, the intensity was acquired by subtracting the averaged background intensity from the corresponding averaged spot intensity. The results from replicate spots were then averaged.

Results and Discussion.

Measurement of Laser Source Power

Figure 4:
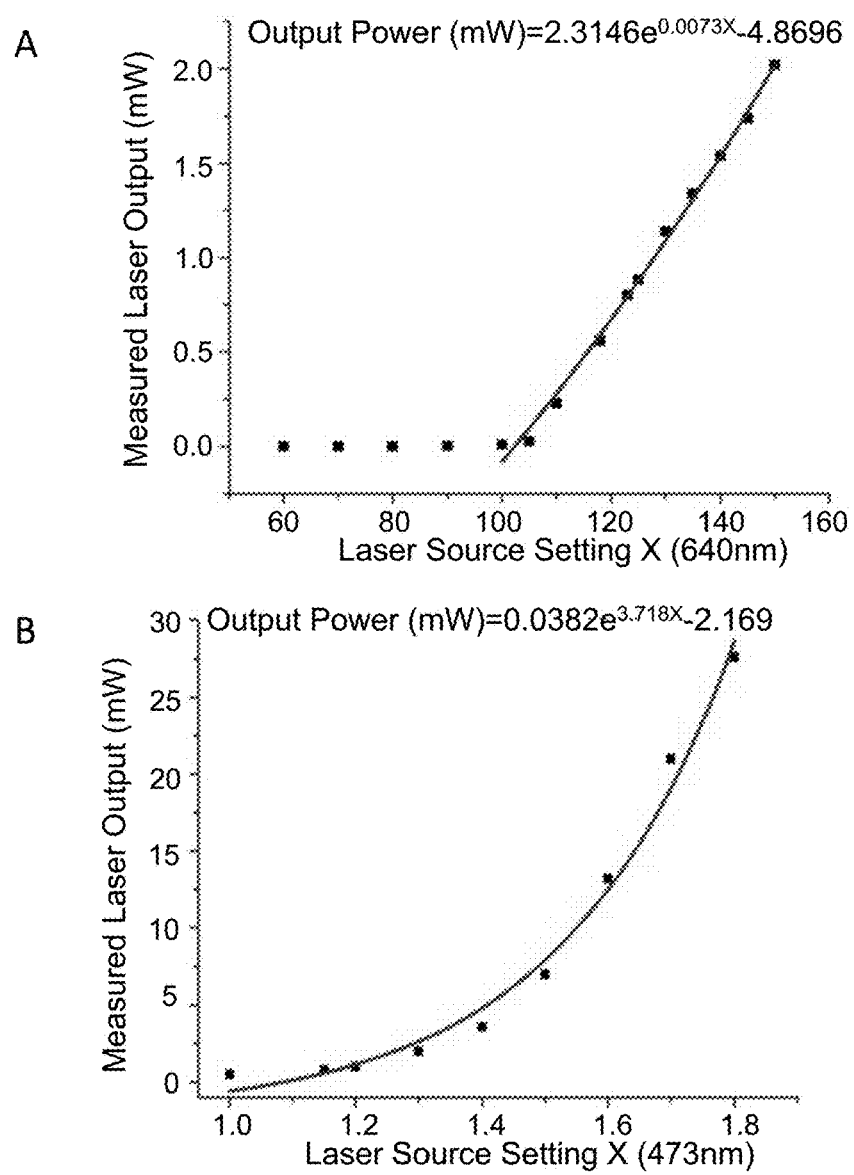
FIG. 4 is a representation of the relationship between laser output power and setting of laser level. (A) 640 nm laser. (B) 473 nm laser.

The laser system only provides a qualitative laser level readout instead of the actual laser power on its LED screen. To precisely control the laser power used for research, calibration curves of laser power with the laser level read out were made using an Ultima LabMaster meter and an EnergyMax-RS sensor from Coherent Inc. Calibrations were performed for both the 640 nm laser and the 473 nm laser. Exponential functions were used to describe the relationship of output power with the level read out, as shown in FIG. 4.

Selection of Imaging Objective

Figure 5:
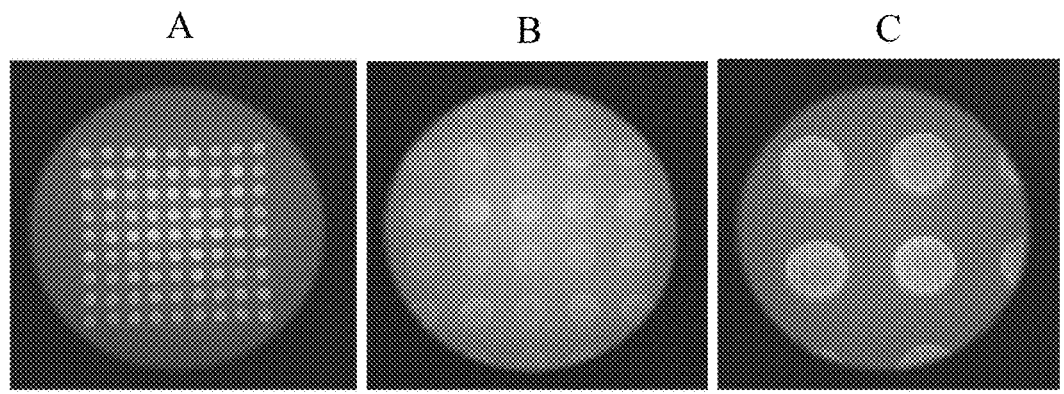
FIG. 5 is a representation of the Total Internal Reflection Fluorescence (TIRF) images at different magnifications, taken with (A) 4× (B) 10× (C) 20× objectives. Images came from the same microarray printed using 10 μmol $L^{-1}$ MO probe, end-modified with fluorescein. The images were taken in 3 mol $L^{-1}$ NaCl solution, all at a laser level of 1.6, exposure time of 1 s, 0 EM gain, and using 473 nm laser excitation.

There were three objective lens available in the TIRF microscope system, with 4×, 10× and 20× magnification. Pictures taken with all three objectives were clear and had the same level of intensities for both the spots and the background (FIG. 5). The objective with 4× magnification was used in all later experiments in order to allow imaging of the most spots.

Background in TIRF

Figure 6:
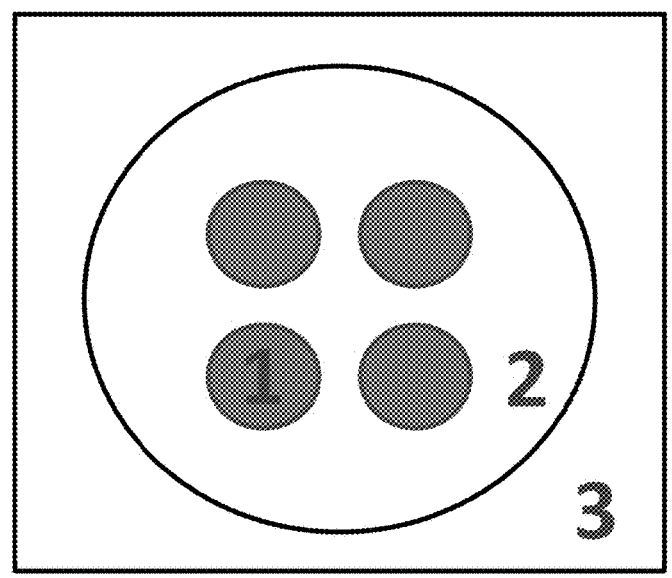
FIG. 6 is a representation of the three locations whose intensities were analyzed to better understand TIRF measurements. The intensities at Location 1, 2 and 3 were used for the hybridized signal, the slide background, and the "preset" background, respectively.

Background is an important factor in TIRF measurements. Although it cannot be entirely eliminated, every effort should be made to adjust the background to as low a value as possible. An alternative way to improve the performance of TIRF measurement would be to increase the signal intensity while keeping background fixed, thus elevating the ratio of signal to background. For this purpose, three locations were compared in TIRF images that were taken with different settings of parameters (FIG. 6). Among these three locations, "1" was a spot, "2" was the area inside of the image window but outside of the spots, and "3" was the area out of the image window but still captured by the camera CCD chip. These three intensities were used for the image signal, image background, and preset background, respectively.

For these TIRF studies, DNA targets end-labeled with Cy5 dye were used. The MO microarray was hybridized with the single-stranded Cy5-modified targets for 16 hours in 0.012 mol $L^{-1}$ phosphate buffer, at room temperature. These conditions supplied relatively stable and sufficiently strong intensities to facilitate the following measurements.

Figure 7:
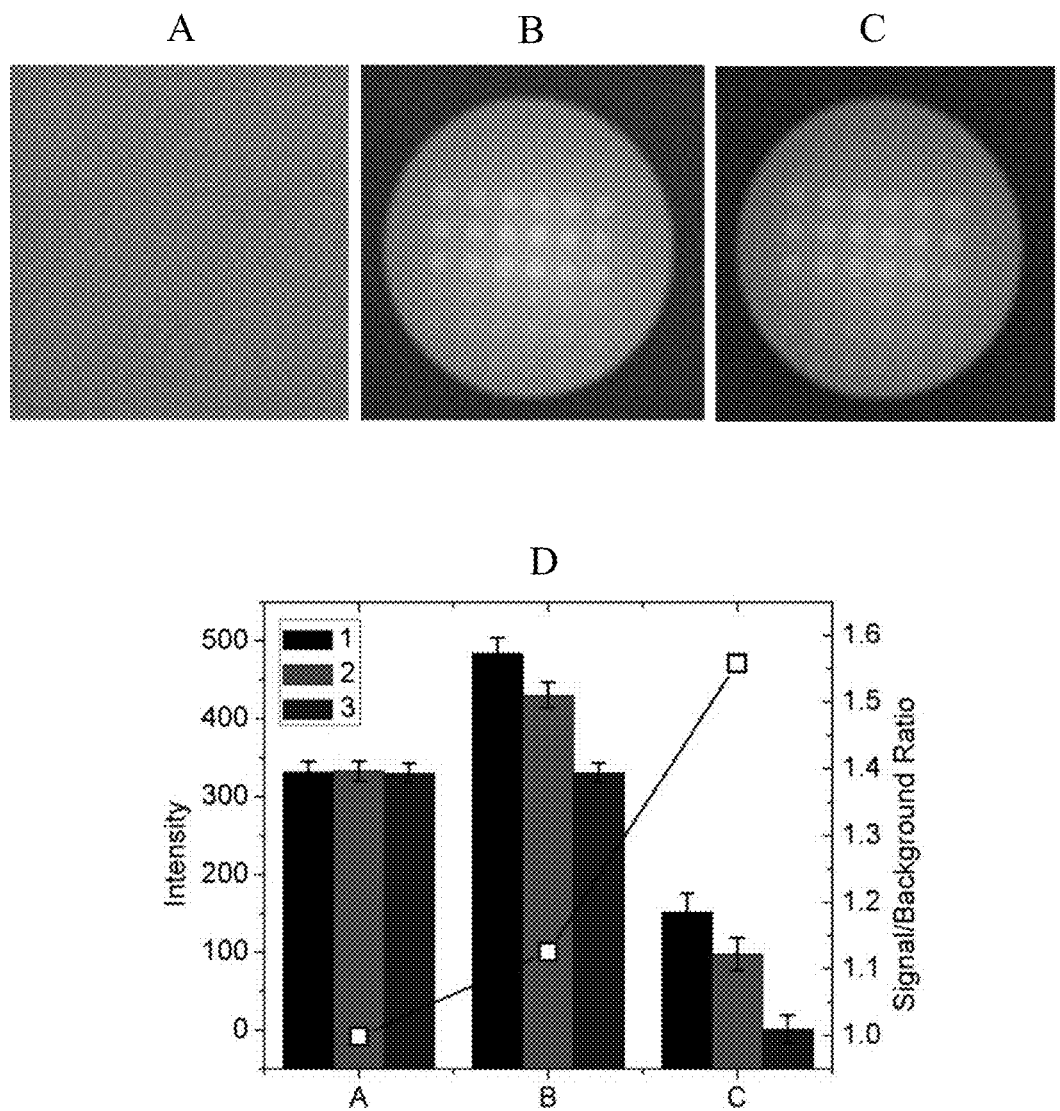
FIG. 7 is a representation of the TIRF images with the laser on (B) and off (A). Image (C) was the result of subtracting (A) from (B). Part (D) presents the intensities corresponding to images (A) through (C). Both (A) and (B) were taken with exposure time of 1 s, 0 EM gain, and at 640 nm laser wavelength. The laser level was set at 118 for (B). The signal/background ratio is indicated by the open squares in (D), and corresponds to the right y-axis. In (D), for each set 1, 2 and 3 are from left to right.

When the laser was turned off (FIG. 7A), a preset background always existed in all three locations, as defined before, with the value of the background the same. After turning on the laser, the image portion of the window lit up from the excited Cy5 dyes and spots could be clearly seen as the result of hybridization (FIG. 7B). The preset background intensities at location 3 were not changed compared to FIG. 7A. Therefore, these signal values around the edges of the image were taken to represent the camera background with the laser off, and as such were subtracted from raw image data, as shown in FIG. 7C.

Figure 8:
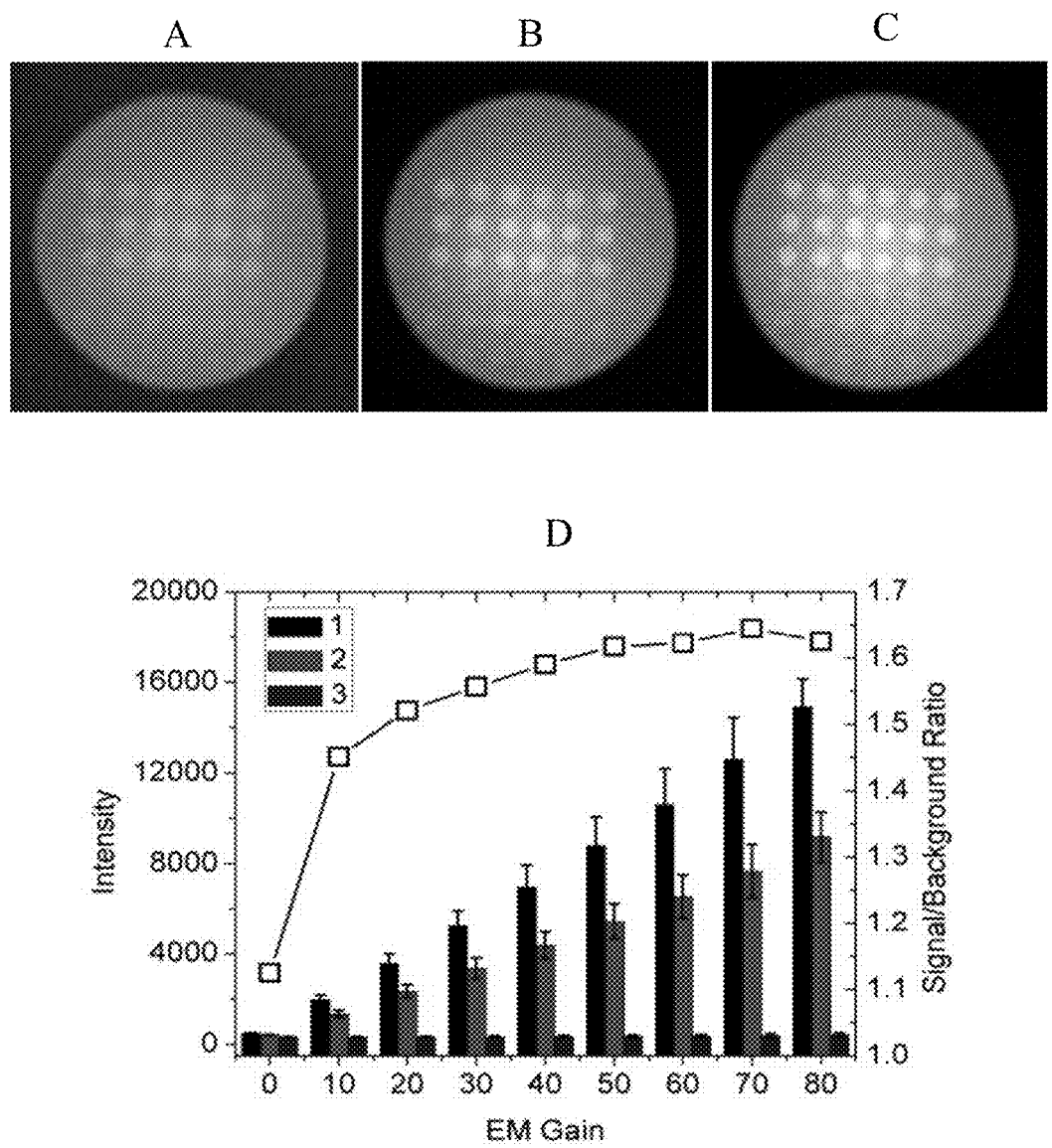
FIG. 8 is a representation of the effects of EM gain. TIRF images were taken at exposure time of 1 s, laser level of 118, and at 640 nm laser wavelength. The EM gain was set at 0 for (A), 40 for (B) and 80 for (C). (D) presents the TIRF intensities with the EM gain ranging from 0 to 80. The signal/background ratio is shown by the open squares, and corresponds to the right y-axis. In (D), for each set 1, 2 and 3 are from left to right.

An obvious increase in the signal/background ratio results from subtraction of the preset background, as seen in FIG. 7D. The same processing was applied to all subsequent TIRF images, except those discussed in the section above Effects of EM Gain Photons that are incident on pixels of a CCD array camera chip are captured and converted to electrons. Electron-Multiplying (EM) gain is the factor used to multiply the signal in electrons in order to increase the sensitivity of the detection and decrease the noise. As shown in FIG. 8, both the signal and background intensities went up with an increase in the EM gain, while the intensities at location 3 stayed at the same level. Therefore, EM gain can be used to decrease impact of preset background on data. Significantly, the signal/background ratio was improved by a higher EM gain, advocating for the use of EM gain especially when the signal is low, though diminishing returns are observed at the highest EM values. However, although higher EM gain increases the sensitivity, it also trades off in the dynamic range. So, to maintain as much dynamic range as possible, the EM gain should be no higher than necessary to measure the signal. In this thesis, most TIRF experiments used 0 EM gain, which was enough to see the microarray spots clearly.

Effects of Exposure Time

Figure 9:
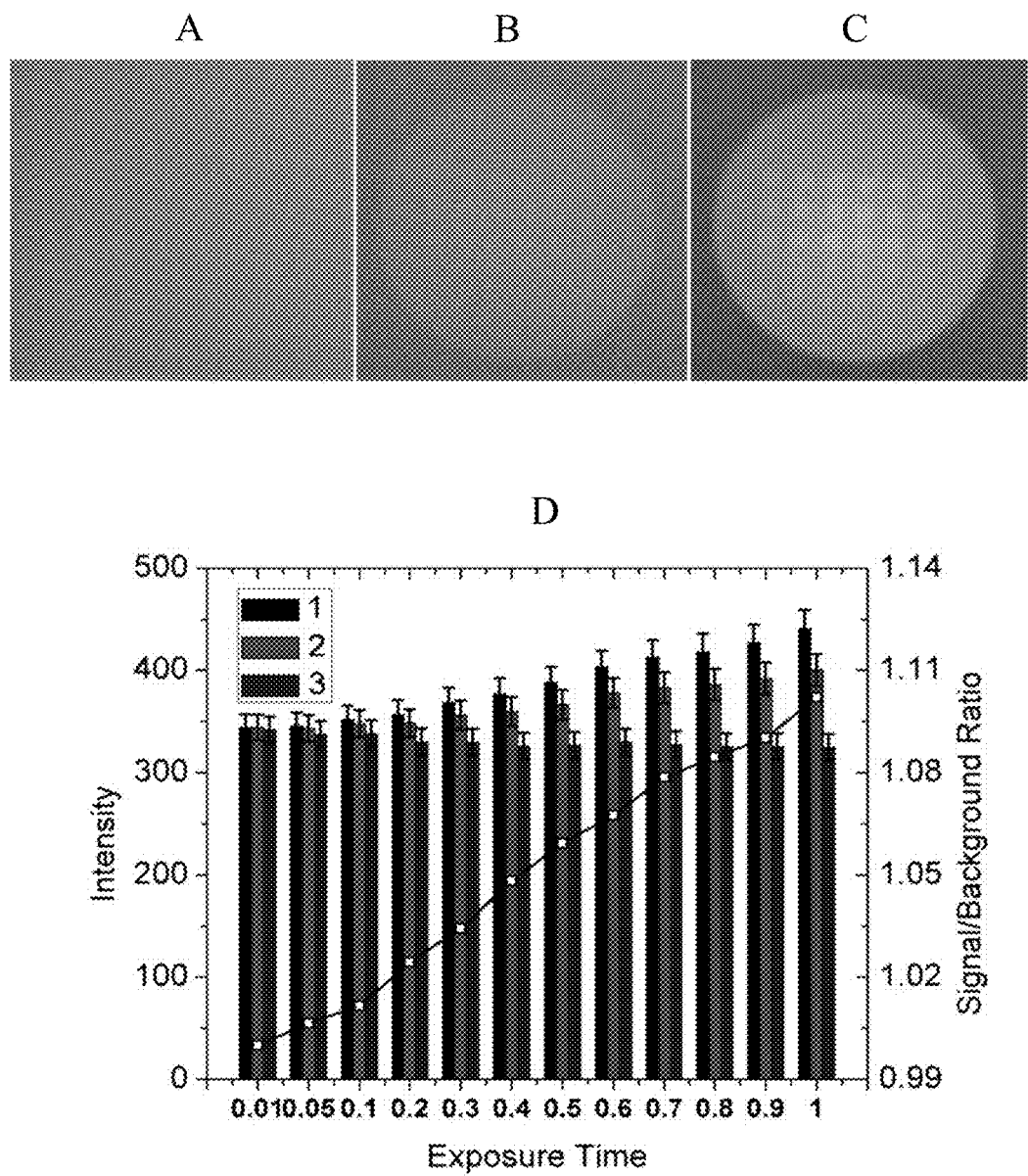
FIG. 9 is a representation of the effects of exposure time. TIRF images were taken at 0 EM gain, laser level of 118 and at 640 nm laser wavelength. The exposure time was set to 0.01, 0.1 and 0.5 s for (A), (B) and (C), respectively. Part (D) shows TIRF intensities for exposure times of 0.01 to 1 s. The signal/background ratio is shown by the open squares, and corresponds to the right y-axis. In (D), for each set 1, 2 and 3 are from left to right.

Exposure time is the time during which the CCD collects light to compose an image Similar to EM gain, longer exposure time resulted in higher signal and background intensities, as the result of more photons being captured (FIG. 9). Interestingly, the intensities at location 3 decreased slightly instead of staying unchanged when exposure time was increased. The reason for this observation is not known. Low contrast images were obtained when exposure time was below 0.1 s; since these conditions would not satisfy requirements for detection they were avoided in later measurements. Although longer exposure times improved the signal/background ratio, they also added time to the experiments and extra risk of photobleaching of fluorescent dyes. An exposure time of 1 s was chosen as a reasonable compromise for all later TIRF experiments.

Effect of Laser Level

Figure 10:
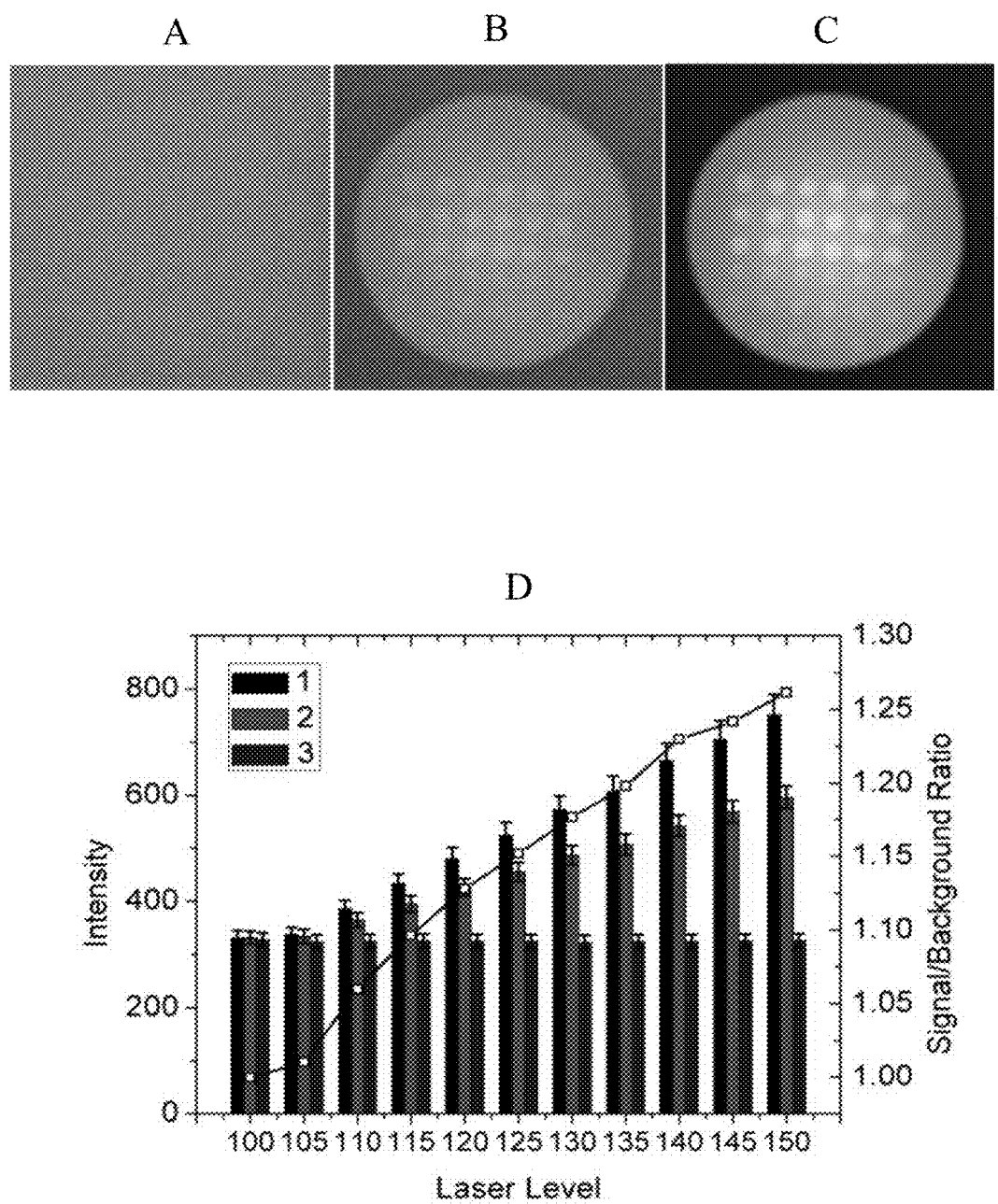
FIG. 10 is a representation of the effects of laser level. TIRF images were taken at 0 EM gain, exposure time of 1 s, and at 640 nm laser wavelength. The laser level was set at 100, 110 and 150 for (A), (B) and (C), respectively. (D) presents the TIRF intensities with the laser level ranging from 100 to 150. The signal/background ratio is indicated by the open squares, and corresponds to the right y-axis. In (D), for each set 1, 2 and 3 are from left to right.

Not surprisingly, stronger laser output increased the signal and background intensities as well as the signal/background ratio (FIG. 10). Given that these images were taken in 0.012 mol $L^{-1}$ phosphate buffer, which was the lowest ionic strength used for research and one expected to result in smallest hybridized amounts due to electrostatic effects associated with accumulation of target charge on the slide, a laser level of 118 was chosen to provide sufficiently clear images while lessening the risk of dye photobleaching.

Fluorescence Un-Quenching Method for Detection of Unlabeled Targets

Figure 11:
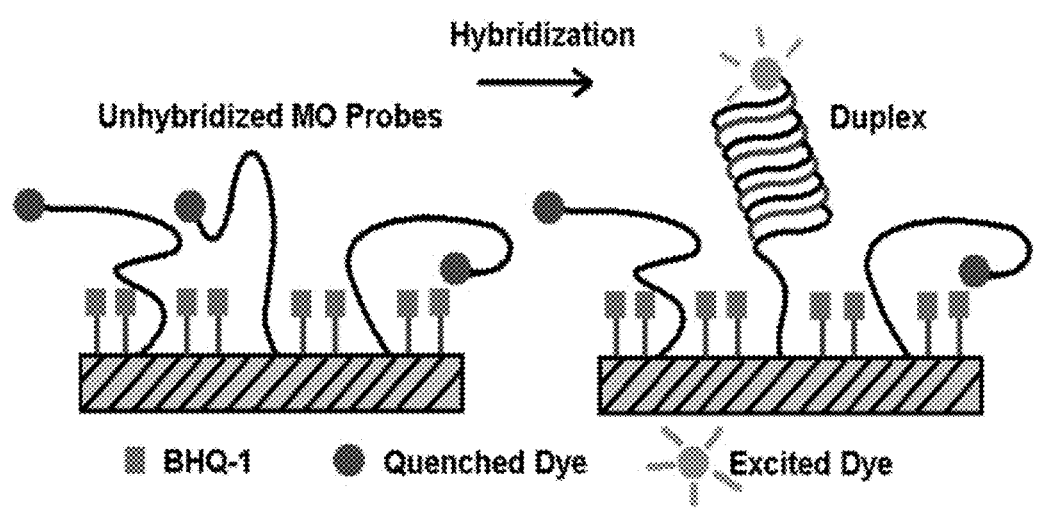
FIG. 11 is a representation of the schematic depiction of the un-quenching approach to detection of unlabeled targets.

In the method of the present invention, unhybridized MO probes sequester near the solid support while hybridized MO probes orient toward the solution likely due to their improved solubility brought on by hybridization with DNA targets. A quencher (acceptor) group is immobilized together with unhybridized MO probes end-modified with a fluorophore (donor) on a microarray slide, which results in quenching. Because the probe conformation is altered by occurrence of hybridization, in that hybridization results in probes orienting toward the solution, hybridization separates the donor/quencher pair so that emission from the probes is increased (FIG. 11). This "un-quenching" method provides an alternative to sample labeling for detection of hybridization. A rather unique advantage of this approach with MO probes is that there is no requirement for sequence pre-design, in contrast to having to use a hairpin or other folded motif with DNA probes as in molecular beacons, surface quenched beacons, or Smart Probes. Instead, with MO probes the approach simply relies on diminished solubility of the uncharged morpholino backbone in the unhybridized state. This simplicity eases experimental design and eliminates potential sources of experimental variability between probe sequences.

Preparation of Quenched Probe Layers

Two ways were considered for preparing MO probe layers quenched by BHQ-1 molecules. In the first probes and BHQ-1 were printed sequentially, while in the second they were printed together in a mixture. The later approach was preferred since it was easier compared to the former, and also tended to produce more uniform spots. Since MO probes were previously found to print well from water and phosphate buffers, initially printing was tested using probe/BHQ-1 mixtures in water and in 0.1 mol $L^{-1}$ pH 9.0 sodium phosphate buffer. However, the amine-BHQ-1 molecule proved poorly soluble in these aqueous solutions. The solubility was therefore improved by adding dimethyl sulfoxide (DMSO) into the printing buffer. Finally, a 75% DMSO solution (v/v) in 0.1 mol $L^{-1}$ pH 9.0 sodium phosphate buffer was chosen as a compromise between realizing good BHQ-1 solubility while maintaining the simplicity of co-immobilized of probe and quencher.

Experiments used microarrays printed from a 1:1 mixture of 10 µmol $L^{-1}$ MO probes and 10 µmol $L^{-1}$ BHQ-1, prepared in 75% DMSO and 25% 0.1 mol $L^{-1}$ pH 9.0 sodium phosphate buffer. 10 µmol $L^{-1}$ MO probes were also printed on the same slide as a control, without BHQ-1. A 3 mol $L^{-1}$ NaCl solution was chosen for hybridization in order to get fast kinetics and increase yields by suppressing electrostatic repulsions between hybridized targets. Images were first taken after filling the TIRF flow cell with this solution, without targets. Next, a freshly prepared hybridization solution with 0.1 µmol $L^{-1}$ DNA targets was added to the TIRF cell, and left at room temperature for 16 hours, at which point additional images were taken.

Figure 12:
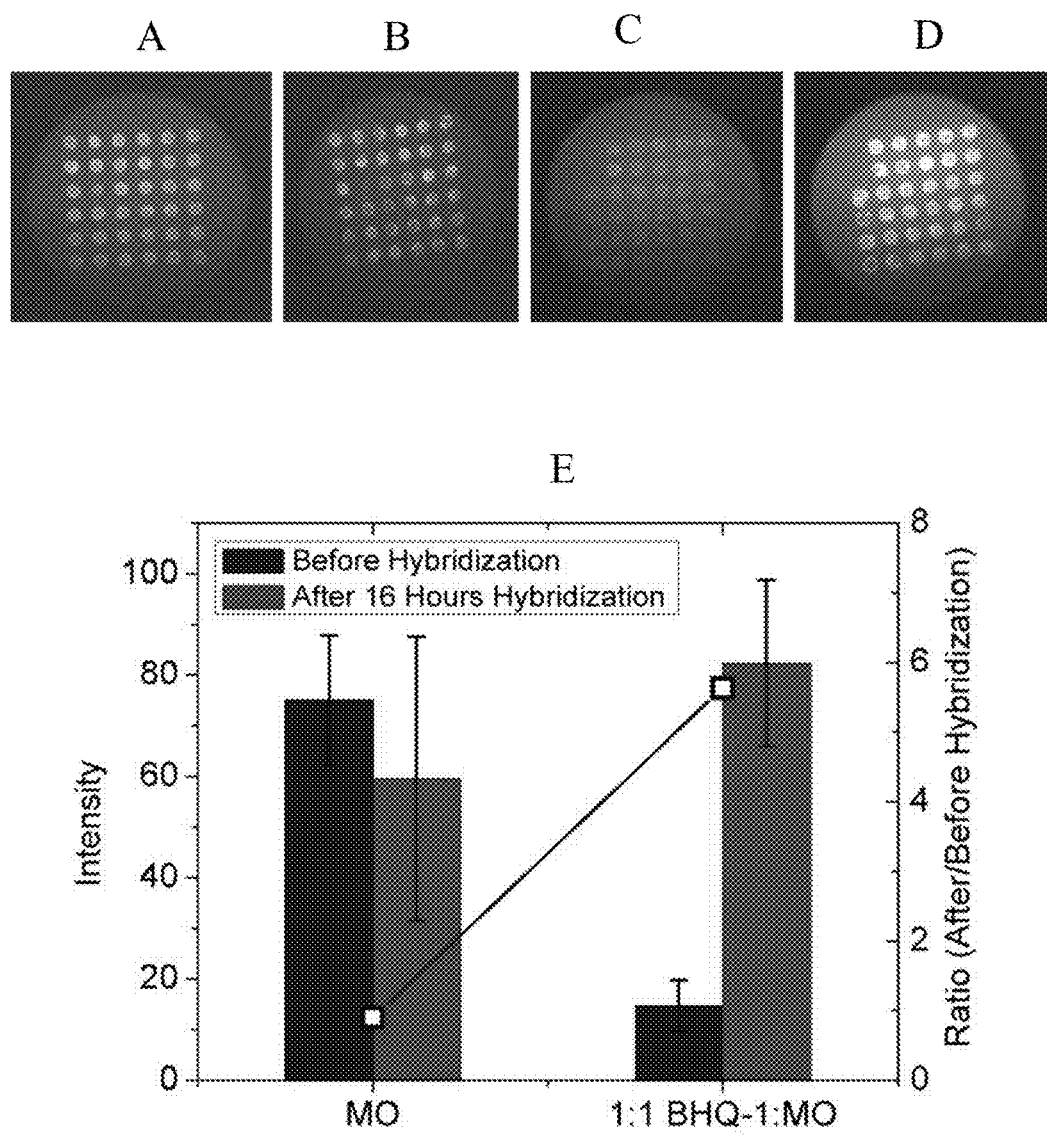
FIG. 12 is a representation of the changes in intensity before and after hybridization using the un-quenching approach. (A) MO probes only, before hybridization. (B) MO probes only, after hybridization. (C) MO/BHQ-1 mixture, before hybridization. (D) MO/BHQ-1 mixture, after hybridization. (E) Averaged TIRF intensities corresponding to the spots in images (A) to (D). All TIRF images were taken in 3 mol $L^{-1}$ NaCl solution at a laser level of 1.6, exposure time of 1 s, 0 EM gain, and at 473 nm laser wavelength. Microarrays were prepared on Vantage aldehyde slides. The ratio of intensity after to before hybridization is shown by the open squares and corresponds to the right y-axis. In (E), for each set 'Before Hybridization', and 'After 16 Hours Hybridization' are from left to right.

As shown in FIG. 12, before adding of target, probe spots were brighter for MO probes printed without BHQ-1 (FIG. 12A) than for their mixture with the quencher (FIG. 12C). The lower mixture intensity is attributed to quenching of fluorescein group on the MO probes by the co-immobilized BHQ-1. After adding unlabeled DNA targets and waiting 16 hours, the fluorescent intensity increased more than 5 times on the MO/BHQ-1 spots while that on the pure MO spots decreased around 20% (FIG. 12E). The increase in intensity for quenched MO probes is attributed to formation of MO/DNA duplexes by hybridization, which brings negative charge to the otherwise neutral MO probes and thus increases their solubility and lifts them up from the microarray surface. The increase in intensity emitted by the probes is therefore a result of this standing-up in response to hybridization with unlabeled target, which separates their fluorescein group from the BHQ-1 quencher immobilized on the surface. The decrease of intensity from Figure A to Figure B could be caused by uncertainties in data analysis. For example, some spots displayed significant non-uniformity in intensity which made precise evaluation of their brightness more difficult. For example, a slight increase (instead of a decrease) of intensity was sometimes calculated for pure MO probes (i.e. without co-immobilized BHQ-1) under the same experimental conditions. These uncertainties are evidenced in the large error bars in FIG. 12.

For the purpose of detecting surface hybridization, it is preferable to have a strong contrast in intensity before and after hybridization. Therefore, the possible ways to optimize the un-quenching approach are to either lower the intensity before hybridization or to increase the intensity after hybridization. All subsequent improvements were based on this line of reasoning.

Effect of the BHQ-1/MO Ratio

Figure 13:
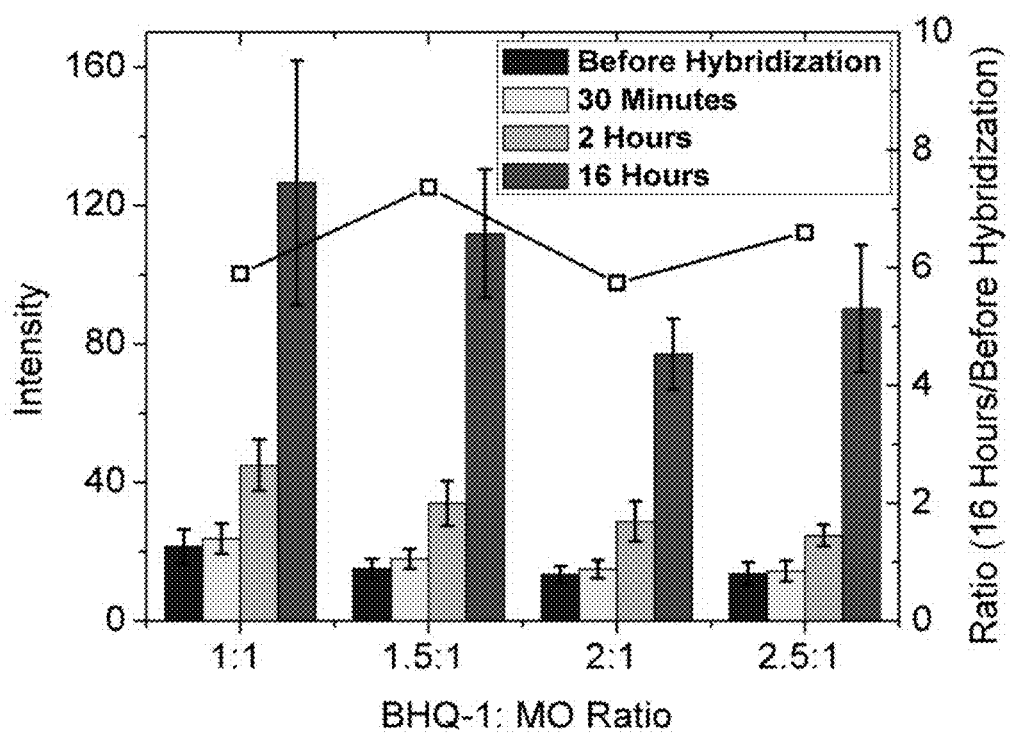
FIG. 13 is a representation of the effects of BHQ-1/MO ratio. All data were collected from TIRF images taken in 3 mol $L^{-1}$ NaCl, at a laser level of 1.6, exposure time of 1 s, 0 EM gain, and at 473 nm laser wavelength. Microarrays were printed on Vantage aldehyde slides. The ratio of intensity after 16 hours of hybridization to that before hybridization is indicated by the open squares, and corresponds to the right y-axis. For each set, from left to right are—'Before Hybridization', '30 minutes', '2 Hours', and '16 Hours'.

The presence and co-immobilization of BHQ-1 on the surface may not only quench probe emission but may also limit the realizable probe coverage. To look at the influence of BHQ-1 concentration used for immobilization, six mixtures with different composition were tested. Since the probes were not fully quenched at a 1:1 BHQ-1/MO ratio, higher ratios were used including 1.5:1, 2:1, 2.5:1, 5:1, and 10:1. As shown in FIG. 13, unhybridized probe spots could be seen except on slides printed from the highest 5:1 and 10:1 BHQ-1/probe ratios. Interestingly, after 16 hours of hybridization, intensities of spots printed using BHQ-1 ratios of less than 5:1 had increased from 5.9 to 7.4 times, while for the 5:1 and 10:1 ratios very little hybridization was observed even if hybridization was prolonged to one week. These results suggested use of a BHQ-1/MO printing ratios of less than 5:1, provided other conditions were kept unchanged. They also proposed that longer incubation time might be needed to increase hybridization signals. Slower hybridization kinetics could be a consequence of attractive fluorescein/BHQ-1 interactions, which may constrain the probes from interacting as effectively with target molecules.

Further Results

Interestingly, when the same 10 µmol $L^{-1}$ 1:1 BHQ-1/MO mixtures were printed on SuperAldehyde slides as opposed to on Vantage aldehyde slides different levels of intensity were realized. The latter slides usually had intensity levels that were around four times higher, after 16 hours hybridization. Therefore, SuperAldehyde slides required longer times to reach the same intensity as a microarray printed on Vantage aldehyde slides.

Figure 14:
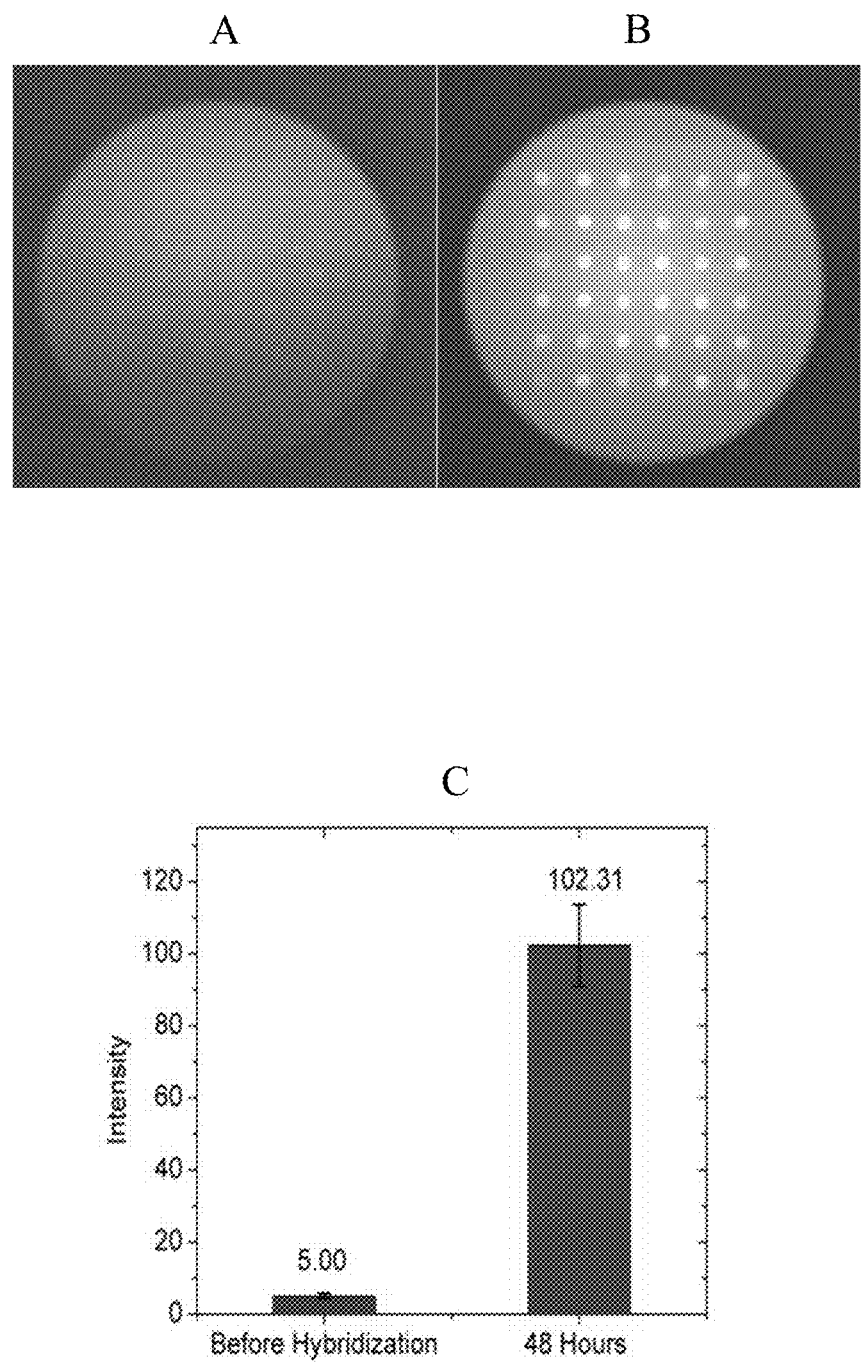
FIG. 14 is a representation of the MO microarray slide (A) before hybridization and (B) after hybridization to 250 nmol $L^{-1}$ target. Part (C) shows the TIRF intensities corresponding to images (A) and (B). TIRF images were taken in 3 mol $L^{-1}$ NaCl solution at a laser level of 1.6, exposure time of 1 s, 0 EM gain, and at 473 nm laser wavelength. Microarrays were printed on SuperAldehyde slides.
Figure 15:
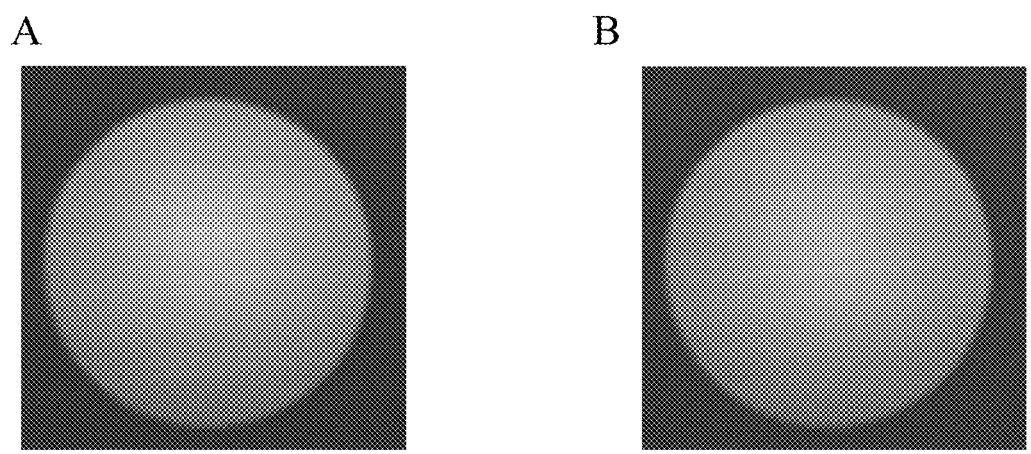
FIG. 15 is a representation of the MO microarray slide (A) before hybridization and (B) after hybridization to 250 nmol $L^{-1}$ non-complementary target. TIRF images were taken in 3 mol $L^{-1}$ NaCl solution at a laser level of 1.6, exposure time of 1 s, 0 EM gain, and at 473 nm laser wavelength. Microarrays were printed on SuperAldehyde slides.

Using SuperAldehyde slides, the un-quenching method was also tested with different target concentrations: 1 nmol $L^{-1}$, 10 nmol $L^{-1}$, and 250 nmol $L^{-1}$, all using slides printed with a 1:1 BHQ-1/MO ratio. Little intensity change was found with 1 nmol $L^{-1}$ and 10 nmol $L^{-1}$ target concentrations after 48 h of hybridization, while a strong increase of spot intensity was observed for a target concentration of 250 nmol $L^{-1}$. In this case, an increase of over 20-fold in intensity was observed (FIG. 14).

An additional experiment was performed to evaluate sequence-specificity of the un-quenching detection method. Using the same hybridization conditions as above, a 20mer DNA non-complementary target was hybridized to the array at a concentration of 250 nmol $L^{-1}$ and for 48 hours. No clear hybridization signal was evident (FIG. 13). This result helped confirm that increases in intensity observed with complementary targets were brought on by sequence-specific hybridization The impact of various parameters on TIRF measurements was discussed in this chapter. The effects of background signals, EM gain, exposure times, and laser level were measured using MO microarrays hybridized with Cy5 labeled DNA targets. TIRF settings that worked reasonably well for microarrays hybridized in 0.012 mol $L^{-1}$ phosphate buffer were subsequently also used for detection under higher ionic strengths. These settings included dialing the laser level to intermediate intensities, using an EM gain of 0, and exposure times of 1 s. Background correction algorithms were also discussed. Lastly, an un-quenching approach to detect hybridization on morpholino microarrays was proposed in the second part of the chapter. This approach was demonstrated to successfully detect unlabeled DNA targets through intensity changes that result from hybridization-induced differences in the conformation of MO probes end-modified with a fluorescein group. Over 20-fold increase in intensity of probe emission was shown possible in response to hybridization.

What is claimed is:

1. A method for detecting the presence or absence of a polynucleotide strand comprising a sequence of interest in a test sample, comprising:
   a) contacting the test sample with a substrate in an aqueous medium, wherein said substrate has fluorescence quenching materials directly attached to its surface, and has a plurality of morpholino strands immobilized on its surface, each morpholino strand of said plurality of morpholino strands having an identical fluorophore attached thereto and comprising a sequence that is complementary to the sequence of interest of the polynucleotide strand, wherein the fluorophore on each morpholino strand of said plurality of morpholino strands and the fluorescence quenching materials are in proximity to each other on said substrate such that, prior to contacting the test sample with said substrate, a fluorescence from the fluorophore of each morpholino strand of said plurality of morpholino strands is quenched by the fluorescence quenching materials and the substrate exhibits a base fluorescence, and after contacting the test sample with said substrate, upon hybridization of one or more morpholino strands of said plurality of morpholino strands to the sequence of interest of the polynucleotide strand, the fluorophore of each of the one or more morpholino strands is sufficiently spatially separated from the quenching materials on said substrate, the fluorescence from the fluorophore of each of the one or more morpholino strands on said substrate is no longer quenched by the fluorescence quenching materials, and the substrate exhibits an increase in the fluorescence from the fluorophore relative to the base fluorescence if the polynucleotide strand comprising a sequence of interest is present in the test sample, and
   b) measuring if there is a change in the fluorescence from the fluorophore on said substrate after contacting the test sample with said substrate, wherein an increase in the fluorescence from the fluorophore of the morpholino strand on the substrate relative to the base fluorescence is indicative of the presence of the polynucleotide strand comprising the sequence of interest in the test sample, and a lack of the increase in the fluorescence from the fluorophore on the substrate relative to the base fluorescence is indicative of the absence of the polynucleotide strand comprising the sequence of interest in the test sample.

2. The method of claim 1, wherein the substrate is a conducting substrate.

3. The method of claim 1, wherein the substrate is a non-conducting substrate having a conducting surface layer.

4. The method of claim 1, wherein the fluorophore on each of the morpholino strands is attached to a position toward the free end of each of the morpholino strands or at the free end of each of the morpholino strands, wherein said free end of each of the morpholino strands is not attached to the substrate.

5. The method of claim 1, wherein each of the morpholino strands does not have a hairpin structure.

6. The method of claim 1, wherein each of the morpholino strands has 15 to 100 bases.

7. A device for detecting the presence or absence of a polynucleotide comprising a sequence of interest in a test sample, comprising: a substrate, wherein said substrate has fluorescence quenching materials directly attached to its surface, and has a plurality of morpholino strands immobilized on its surface, each morpholino strand of said plurality of morpholino strands comprising a sequence that can hybridize to the sequence of interest of the polynucleotide and having an identical fluorophore attached thereto, wherein the fluorophore on each morpholino strand of said plurality of morpholino strands and the fluorescence quenching materials are in proximity to each other on said substrate such that, prior to contacting the test sample with said substrate, a fluorescence from the fluorophore of each morpholino strand of said plurality of morpholino strands is quenched by the fluorescence quenching materials on said substrate and the substrate exhibits a base fluorescence, and upon hybridization of one or more morpholino strands of said plurality of morpholino strands to the sequence of interest of the polynucleotide strand, the fluorophore of each of the one or more morpholino strands is sufficiently spatially separated from the quenching materials on said substrate, the fluorescence from the fluorophore of each of the one or more morpholino strands on said substrate is no longer quenched by the fluorescence quenching materials and the substrate exhibits an increase in the fluorescence from the fluorophore relative to the base fluorescence if the polynucleotide strand comprising a sequence of interest is present in the test sample.

8. The device of claim 7, wherein the fluorophore on each of the morpholino strands is attached to a position toward the free end of each of the morpholino strands or at the free end of each of the morpholino strands, wherein said free end of each of the morpholino strands is not attached to the substrate.

9. The device of claim 7, wherein the substrate is a conducting substrate.

10. The device of claim 7, wherein the substrate is a non-conducting substrate having a conducting surface layer.

11. The device of claim 7, wherein each of the morpholino strands does not have a region that can form a hairpin structure.

12. The device of claim 7, wherein each of the morpholino strands has 15 to 100 bases.

\* \* \* \* \*

SEQUENCE LISTING

<160> NUMBER OF SEQ ID NOS: 2

<210> SEQ ID NO 1
<211> LENGTH: 25
<212> TYPE: DNA
<213> ORGANISM: artificial sequence
<220> FEATURE:
<223> OTHER INFORMATION: pimer

<400> SEQUENCE: 1
gtagctaatg atgtggcatc ggttg                                          25

<210> SEQ ID NO 2
<211> LENGTH: 25
<212> TYPE: DNA
<213> ORGANISM: artificial sequence
<220> FEATURE:
<223> OTHER INFORMATION: primer

<400> SEQUENCE: 2
tagctaatga tgtggcatcg gttgc                                          25